US00PP28507P3

(12) United States Plant Patent
Lescow

(10) Patent No.: US PP28,507 P3
(45) Date of Patent: Oct. 10, 2017

(54) *THUJA* PLANT NAMED 'LESDASMA'

(50) Latin Name: *Thuja occidentalis*
Varietal Denomination: Lesdasma

(71) Applicant: Jan Lescow, Bokholt-Hanredder (DE)

(72) Inventor: Jan Lescow, Bokholt-Hanredder (DE)

( * ) Notice: Subject to any disclaimer, the term of this patent is extended or adjusted under 35 U.S.C. 154(b) by 92 days.

(21) Appl. No.: 14/545,325

(22) Filed: Apr. 22, 2015

(65) Prior Publication Data

US 2016/0316600 P1 Oct. 27, 2016

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

Upov Pluto Plant Variety Database Aug. 10, 2016, retrieved on Aug. 29, 2016, retrieved from the Internet at <http://www.upov.int/pluto/en/index.jsp> 1 page.*

* cited by examiner

*Primary Examiner* — June Hwu
(74) *Attorney, Agent, or Firm* — James M. Weatherly; Bethany R. Roahrig; Cochran Freund & Young, LLC

(57) ABSTRACT

A new *Thuja* plant particularly distinguished by having green to dark green leaf color, dense branching and a slender conical plant habit, is disclosed.

2 Drawing Sheets

Genus and species: *Thuja occidentalis*.
Variety denomination: 'Lesdasma'.

BACKGROUND OF THE NEW PLANT

The present invention comprises a new and distinct variety of *Thuja*, botanically known as *Thuja occidentalis* and hereinafter referred to by the variety name 'Lesdasma'. 'Lesdasma' originated from a whole plant mutation discovered in an outdoor nursery located in Bokholt-Hanredder, Schleswig-Holstein, Germany in an open field of the commercial *Thuja* variety 'Smaragd' (patent status unknown).

In approximately May of 1998, a whole plant mutation of *Thuja* variety 'Smaragd' was discovered in Bokholt-Hanredder, Germany. The whole plant mutation was selected in approximately September of 2002 in Bokholt-Hanredder, Germany and grown for evaluation. The mutation was subsequently named 'Lesdasma'. In September, 2004, 'Lesdasma' was first vegetatively propagated by branch cuttings in Bokholt-Hanredder, Germany from one to two year old branches. 'Lesdasma' was found to reproduce true to type in successive generations of asexual propagation via branch cuttings.

CROSS REFERENCE TO RELATED APPLICATION

Plant Breeder's Rights for 'Lesdasma' were applied for in the European Community on Nov. 4, 2011, Application No. 2011/2655. 'Lesdasma' has not been made publicly available or sold more than one year prior to the priority date of this application.

SUMMARY

The following are the most outstanding and distinguishing characteristics of this new variety when grown under normal horticultural practices in Aarslev, Denmark.

1. Dark green fall to winter leaf color;
2. Dense branching; and
3. Slender conical plant habit.

DESCRIPTION OF THE PHOTOGRAPHS

This new *Thuja* plant is illustrated by the accompanying photographs, which shows plant grown in soil and then potted. The photographs are of an eight (8) year-old plant grown outdoors in Bokholt-Hanredder, Germany in October 2011. The colors shown are as true as can be reasonably obtained by conventional photographic procedures.

DESCRIPTION OF THE NEW VARIETY

Figure 1:
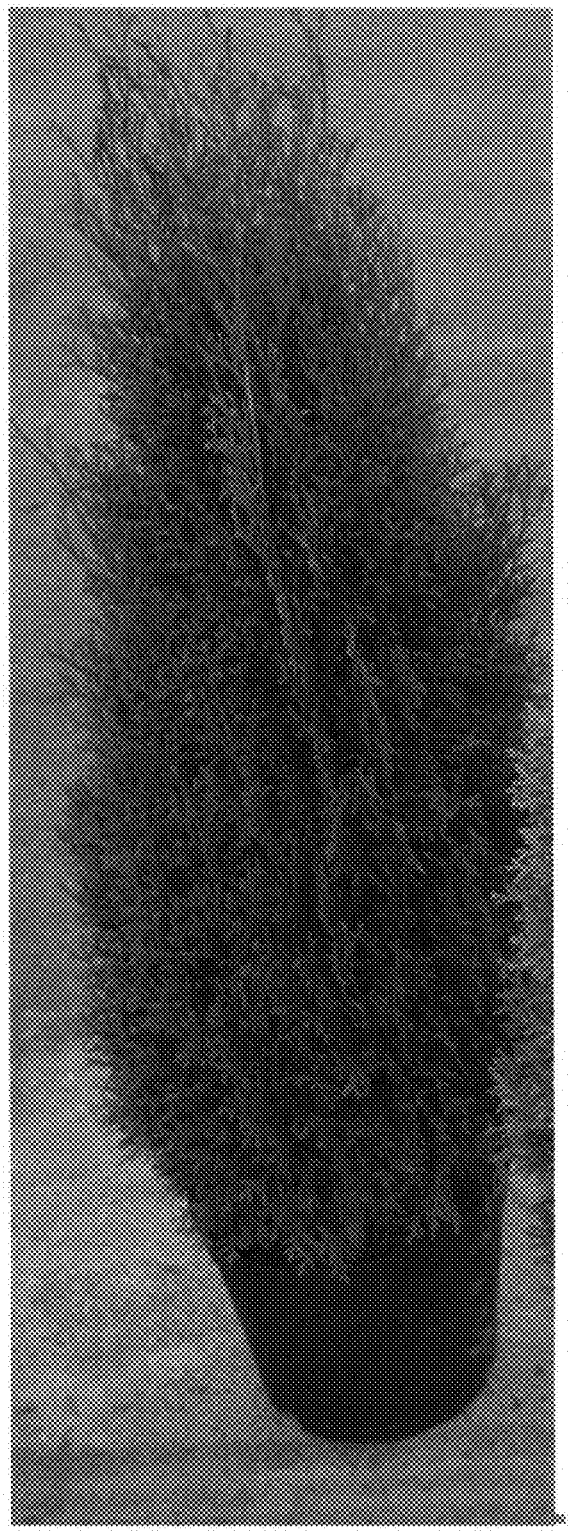
FIG. 1 shows the cultivar *Thuja* 'Lesdasma' grown in a pot.
Figure 2:
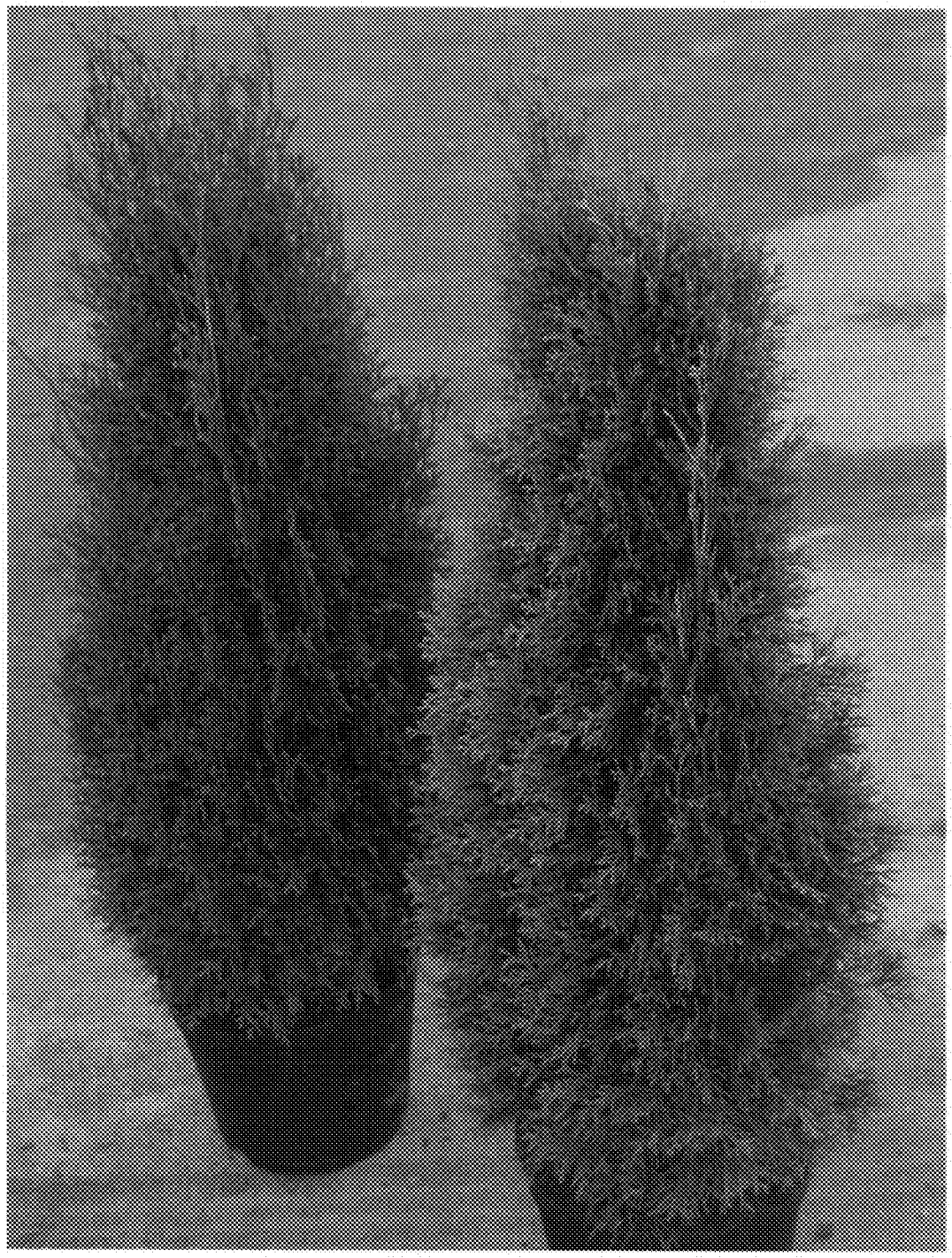
FIG. 2 shows FIG. 1 expanded to show a conventional *Thuja* 'Smaragd' on the right and the cultivar *Thuja* 'Lesdasma' on the left.

The following detailed descriptions set forth the distinctive characteristics of 'Lesdasma'. The data which define these characteristics were collected from asexual reproductions carried out in Aarslev, Denmark. Data was collected on plants 3 to 6 years of age. Color references are to The R.H.S. Colour Chart of The Royal Horticultural Society of London (R.H.S.), $5^{th}$ edition (2007), except where otherwise noted.

Classification:

*Family*.—Cupressaceae.
*Genus*.—*Thuja*.
*Species*.—*occidentalis*.
*Common name*.—Arborvitae, American Arborvitae, Northern Whitecedar.

Parentage:

*Mutation parent*.—The commercial line *Thuja* 'Smaragd' (not patented).

Plant:

*Type*.—Conifer Propagation type: Cutting.

*Shape*.—Slender conic.

*Density*.—Medium to dense.

*Growth rate*.—Slow to medium.

*Use*.—*Thuja occidentalis* 'Lesdasma' is a medium growing coniferous shrub that can be used as a solitary garden plant or grouped as a hedge planting.

*Height* (8 *year-old plant*).—85.0 cm.

*Width* (*spread*) (8 *year-old plant*).—38.0 cm.

*Vigor*.—Medium.

*Average growth rate*.—15.0 cm per season.

*Time to initiate roots during the summer*.—Approximately 60 days.

*Number of days to produce a rooted young plant during the summer*.—270 days.

*Time to a finished plant*.—24 months.

Roots:

*Density*.—Densely growing, fine roots.

*Branching*.—Dense.

*Thickness*.—Fine.

*Texture*.—Similar to *Thuja occidentalis*.

Stem (trunk):

*Diameter*.—1.5 cm to 2.0 cm (measured at 5.0 cm from soil).

*Texture*.—Smooth when young, but develops narrow, irregularly shredding bark over time.

*Mature trunk bark color*.—RHS 200B (The R.H.S. Colour Chart of The Royal Horticultural Society of London (R.H.S.), 6th edition).

Lateral branches:

*Branching habit*.—Dense.

*Type*.—Upright aspect, linear, alternate. Densely divided with many secondary and tertiary branchlets that are flattened and held in a vertical orientation.

*Attitude*.—Erect.

*Number of lateral branches per plant* (*average*).—Medium to many.

*Diameter* (*average*).—0.4 cm.

*Length of internode* (*average*).—4.0 cm.

*Texture*.—Smooth.

*Strength*.—Flexible.

*Pubescence*.—Absent.

*Color*.—Between RHS N199B and RHS N199C (The R.H.S. Colour Chart of The Royal Horticultural Society of London (R.H.S.), 6th edition).

*Branchlets*.—Quantity: Many. Average length including foliage: 14.4 cm. Average diameter of stem: 0.19 cm. Average width including foliage: 8.0 cm. Color: Between RHS 166B and RHS 166C; white markings absent (The R.H.S. Colour Chart of The Royal Horticultural Society of London (R.H.S.), 6th edition).

Leaves:

*Arrangement*.—Opposite and simple.

*Type*.—Flattened scale-like leaves, appressed along branches and branchlets.

*Fragrance*.—Present, aromatic and cedar-like.

*Shape*.—Rounded.

*Length*.—Average is 2.75 mm.

*Width*.—Narrow to medium; average is 1.54 mm.

*Thickness*.—Thin.

*Axis*.—Straight.

*Apex*.—Acute.

*Attitude of spray*.—Oblique.

*Color* (*The R.H.S. Colour Chart of The Royal Horticultural Society of London* (*R.H.S.*), *6th edition*).—In spring and fall: Upper side: Green; RHS 144A to RHS 144B. Lower side: Green; RHS 144A. In summer: Upper side: Green; RHS 143A to RHS 141A. Lower side: Green; Between RHS NN137A and RHS NN137B. In winter: Upper side: Dark Green; RHS 152B to RHS 146B. Lower side: Dark Green; between RHS 146A and RHS 146B.

*Variegation*.—Absent.

*Durability to stresses*.—High, tolerates urban climates.

*Venation*.—None.

*Glands*.—Absent or few.

*Glossiness*.—Weak.

*Fragrance*.—Typical fragrance of *Thuja*.

Cone and seed production: Not observed.

Disease and insect resistance: No disease or insect resistance observed.

COMPARISON WITH PARENTAL LINE AND KNOWN VARIETY

'Lesdasma' is distinguished from its parent as described in Table 1:

TABLE 1

Comparison with Parental Line

| Trait | 'Lesdasma' | 'Smaragd' |
|---|---|---|
| Leaf color (spring/fall, summer, winter) | Green to Dark green | Light green |
| Growth (branches) | Dense | Very dense |
| Habit | Slender conic | Conic |

'Lesdasma' is similar to the commercial *Thuja* 'Silvanus 1' (U.S. Plant Pat. No. 18,036). Differences between the varieties are described in Table 2.

TABLE 2

Comparison with Known Variety

| Trait | 'Lesdasma' | 'Silvanus 1' |
|---|---|---|
| Vigor | Slow to medium | Slow |
| Leaf thickness | Thin | Thin to medium |
| Leaf width | Narrow to medium | Narrow |
| Habit | Slender conic | Ovoid |

I claim:

1. A new and distinct cultivar of *Thuja* plant named 'Lesdasma' as described and illustrated herein.

* * * * *